(12) United States Patent
Romans

(10) Patent No.: US 7,388,124 B2
(45) Date of Patent: *Jun. 17, 2008

(54) NON-TRAUMATIC MODEL FOR NEUROGENIC PAIN

(76) Inventor: Mary Hannaman Romans, P.O. Box 100996, Fort Worth, TX (US) 76185

(*) Notice: Subject to any disclaimer, the term of this patent is extended or adjusted under 35 U.S.C. 154(b) by 0 days.

This patent is subject to a terminal disclaimer.

(21) Appl. No.: 11/384,856

(22) Filed: Mar. 20, 2006

(65) Prior Publication Data

US 2006/0161998 A1 Jul. 20, 2006

Related U.S. Application Data

(63) Continuation-in-part of application No. 09/800,870, filed on Mar. 7, 2001, now Pat. No. 7,015,371.

(51) Int. Cl.
- *A01K 67/00* (2006.01)
- *A01K 67/033* (2006.01)
- *A61K 38/00* (2006.01)
- *G01N 33/00* (2006.01)

(52) U.S. Cl. .............. 800/9; 800/8; 800/3; 514/21

(58) Field of Classification Search ............. None
See application file for complete search history.

(56) References Cited

OTHER PUBLICATIONS

Field, MJ et al, 1999, Detection of static and dynamic components of mechanical allodynia in rat models of neuropathic pain:are they signalled by distinct primary neurons, Pain, 83:303-311.*
LoPinto, C et al, 2006, Cepalagia, 26:852-856.*
Wang, L.X. 2003, Animal and cellular models of chronix pain. Adv. Drug Deliv. Rev. vol. 55, pp. 949-965.
Petersen, K.L. 2001, Effect of remifentanil on pain and secondary hyperalgesis associated with the heat-capsaicin sinsitization model in healthy volunteers, Anesthesiology, vol. 94, pp. 15-20.
Lublin, J. 1998, Carpal tunnel syndrome: a review of initial diagnosis and treatment for the OB/GYN, Prim Care Update Ob/Gyns, vol. 5, pp. 280-285.
Eliav, E., 1999, Neuropathic pain from an experimental neuritis of the rat sciatic nerve, Pain, vol. 83, pp. 169-182.
Keeton, W and Gould, J., Biological Science, 4th edition, W.W. Norton and Company, paragraph bridging pp. 458-459, 1986.
Lundborg, G. 1982, Median nerve compression in the carpal tunnel-Functional response to experimentally induced controlled pressure, Journal of Hand Surgery, vol. 1, pp. 252-259.
Wall, 1996, "Transgenic Livestock: Progress and Prospects for the Future", Theriogenology, vol. 45, pp. 57-68.
Houdebine, 1994, "Production of Pharmaceutical Proteins from Transgenic Animals", J. Biotech. vol. 34, pp. 269-287.
Reyna, 1999, "Biogenic Animal Model of Chronic Pain: A Nontraumatic Model", ICLAS, Palma de Malloren, May 26-28, p. 226.
Ford, 1986, "Histologic Studies on the Fate of Soluble Collagen Injected into Canine Vocal folds", Laryngoscope, vol. 96, pp. 1248-1257.
Allodynia, Stedman's Medical Dictionary, online http://www.stednians.com, 2008 http://216.251.232.159/semdweb/internetsomd/ASP/1526727.asp.
Hyperalgesia, Stedman's Medical Dictionary,online http://www.stedmans.com, 2008.
Moss et al. 2002, "A Role of the Ubiquitin-Proteasome System in Neuropathic Pain", J. of Neuroscience, 22(4):1363-1372.
Reeve et al. 1998, "Spinal Effects of Bicuculline: Modulation of an Allodynia-Like State by an $A_1$-Receptor Agonist, Morphine, and an NMDA-Receptor Antagonist", J. Neurophysiol., 79(3):1494-1507.
Suzuki et al., 2004, "ReN-1869 [(R)-1-(3-(10,11-Dihydro-5$H$-dibenzo[$a,d$]cyclohepten-5-ylidene)-1-propyl)-3-piperidine Carboxylic Acid], a Novel Histamine H1 Receptor Antagonist, Produces Potent and Selective Antinociceptive Effects on Dorsal Horn Neurons after Inflammation and Neuropathy", Pharmacol Exp Ther., 309(3):1230-1238.
Senapati et al. 2005, "Electrical Stimulation of the Anterior Cigulate Cortex Reduces Responses of Rat Dorsal Horn Neurons to Mechanical Stimuli", J Neurophysiol., 94(1):845-851.
Zhuo and Gebhart, 2002, "Modulation of Noxious and Non-Noxious Spinal Mechanical Transmission From the Rostral Medial Medulla in the Rat", J Neurophysiol., 88(6):2928-41.

* cited by examiner

*Primary Examiner*—Valarie Bertoglio
(74) *Attorney, Agent, or Firm*—Howrey LLP

(57) ABSTRACT

A method for producing a non-human mammalian model for neurogenic pain is provided, which includes altering a peripheral nerve of a non-human mammal by non-surgically placing a gel substance into the fascial tunnel through which the peripheral nerve passes. The placement of the gel substance leads to one or more pain behaviors thereby producing the pain model. Also provided is a non-human mammalian model for neurogenic pain so produced. Further provided is a method for screening a treatment or a therapeutic agent for efficacy in treating neurogenic pain as well as a method for screening an analgesic agent for analgesic effect in neurogenic pain.

15 Claims, No Drawings

NON-TRAUMATIC MODEL FOR NEUROGENIC PAIN

This application is a continuation-in-part of U.S. patent application Ser. No. 09/800,870, filed on Mar. 7, 2001, now U.S. Pat. No. 7,015,371, the entire contents of which are incorporated herein by reference.

FIELD OF THE INVENTION

The present invention generally relates to neurogenic pain and animal models for neurogenic pain. In particular, the present invention relates to an animal model for neurogenic pain and a method for generating such model. In addition, the present invention also relates to a method for screening agents or treatments effective in treating neurogenic pain as well as a method for screening analgesic agents for analgesic effects in neurogenic pain. Furthermore, the present invention relates to a composition effective for treating neurogenic pain.

BACKGROUND OF THE INVENTION

The nervous system routinely sends coded signals that result in sensation. Certain types of lesions to either the central or peripheral nervous system can result in an alteration of sensation which leads to pain. Research into persistent or chronic pain has focused mainly on the spinal cord and brain, with little being done to examine the peripheral nervous system. This is so even though researchers and physicians who treat persistent pain syndromes believe that the peripheral nervous system is the origin of much of the pain that needs treatment.

Even though the peripheral nervous system may be considered as the origin of the majority of persistent pain, such pain usually has no known cause. No evidence exists of nerve damage, inflammation or of a biophysical etiology. The lack of knowledge concerning the cause of persistent pain hinders research and development of therapeutics to treat such pain. Many researchers refer to the puzzle of pain when referring to persistent neurogenic pain. The cause of neurogenic pain is only well-defined when there has been a history of direct trauma to a nerve. The majority of persistent neural pain, however, develops slowly near an area of soft tissue injury, without evidence of direct trauma.

Neurogenic pain is pain attributed to a functional disturbance of a nerve or a transitory pertubation, which can occur as a result of alterations and/or injury to nerves. It may occur by a variety of mechanisms including irritation, injury and compression of the peripheral nerves. The symptoms of neurogenic pain may include a burning sensation, tingling, or electric-shock-like feelings that may be triggered by even a very light touch. Human persistent pain conditions are organized into two categories: Complex Regional Pain Syndrome I (CRPS I) and Complex Regional Pain Syndrome II (CRPS II). CRPS I refers to pain without obvious nerve injury, while CRPS II refers to pain with known nerve injury (Merskey and Bogduk, 1994, Classification of Chronic Pain, Second Edition, IASP Press). Current animal models do not represent CRPS I, persistent pain without obvious nerve injury.

Any physical change to a nerve can cause physiologic alterations depending on the nerve's receptor organ and the direction of its electric current. For example, pressure on a nerve is capable of causing nondestructive (non-traumatic) alterations or injury to the nerve that can be seen as changes of characteristics such as in the blood flow of the vasonavorum, in the accumulation of edema within the nerve, in the axonal flow, and in the electrical conductivity and immune cell populations of the nerve. Such changes of pressure on a nerve can result in observable signs and symptoms of nondestructive nerve injury such as behavioral changes of pain with increased sensitivity to light touch and painful sharp touch, licking of paws, edema, and increased sensitivity to heat and cold. Other physical examination signs commonly seen that are associated with more traumatic and/or destructive nerve injury would include sensory numbness and/or hyperalgesia to heat, paw edema, dragging of limb, chewing of paws, tremors, spasms, weakness due to neural loss, and/or paralysis. The functional change in a nerve may depend on the area and force of pressure applied and the resultant changes in extracellular matrix, glial cells, blood flow, lymph circulation, and electrical conductance secondary to the pressure. The consequent alterations in a nerve and their subsequent sensory and behavioral changes may not be immediate, as is seen in a quick high-pressure crush-type injury. In fact, there may be a delay of a few days to several weeks before the onset of neurogenic pain after a tissue injury in humans. Such delayed onset pain conditions can include cervical whiplash, post-traumatic regional persistent pain, post-surgical pain and repetitive trauma syndromes such as radial neuritis. Therefore, animal models of nerve pain must consider the physiological changes occurring in tissue during healing and remodeling after a soft tissue injury, since such changes can result in the delayed onset of persistent neurogenic pain.

Current animal models have focused on production of pain through strategies such as irritating, cutting, crushing, ligating, or freezing the nerves in order to model a human peripheral nerve injury with neuropathic pain. However, such injuries are rarely noted as an initiating etiology in humans. In clinical practice the majority of occupational injuries involving such direct trauma as crush, nerve transection or burns heal without developing chronic neurogenic or neuropathic pain conditions. Examples of animal models using direct neural trauma include: use of chemical irritants injected into a limb or paw (Liu-Chen, et al. 1991, Eur. J. Pharmacol. 15:195-202); transient nerve crush by compressing the nerve with a micro-cuff (Attal, et al. 1994, Pain 59:301-312); freezing the sciatic nerve using the technique of sciatic cryoneurolysis (Willenbring, et al. 1994, Pain 58:135-140; Wagner, et al. 1995, Physiol. Behav. 58:37-41); sciatic nerve partial injury induced by dissecting the nerve lengthwise into two pieces and only ligating one (Seltzer, et al. 1990, Pain 43:205-218); sciatic nerve partial cut where only a part of the nerve is transected (Dougherty, et al. 1992, Brain Res. 20:109-115); sciatic nerve full cut where the nerve is completely transected (Kingery, et al. 1999, Pain 80:555-566); nerve root ligatures where the lumbar nerve roots are ligated (Kim, and Chung, 1992, Pain 50:355-363; Choi, et al. 1994, Pain 59:369-376); polyethylene cuffs to produce a compression injury (Mosconi and Kruger, 1996, Pain 64:37-57); use of hemostatic oxidized cellulose that on one side was saturated with an inflammatory stimulus, carrageenan, or complete Freund's adjuvant (Eliav, et al. 1999, Pain 83:169-182); bee venom injected into rat paw (Chen, et al. 2000, Neurosci. Lett. 284:45-48); scalding of rat paw (Lofgren, et al. 1997, Acta Physiol. Scand. 161:289-294); photochemically-induced laser lesion of sciatic nerve (Gazelius, et al. 1996, Neuroreport. 4:2619-2623); use of zymosan on the sciatic nerve (Chacur, et al. 2000, American Pain Society Poster Presentation); and a spared nerve injury model where two or three terminal branches of the sciatic nerve are transected (Decosterd and Woolf, 2000, Pain 87:149-158). All of these animal models rely on production of a destructive nerve injury through direct nerve trauma, irritation, or an acute immune response. A model extensively studied for chronic pain is the Chronic Constriction Injury (CCI) model where a sciatic nerve injury is induced by tying four chromic gut sutures loosely around the nerve (Bennett and Xie, 1998, Pain 33:87-107). However, this model produces animals that have difficulty walking due to the immediate, acute pain and swelling seen in the leg on which the procedure is performed. As a result, special attention to animal care is needed for these animals for 3 to 4 days. None of the current models create persistent neurogenic pain in animals that are fully ambulatory within minutes of the procedure and require no special care.

In addition, current animal models of neuropathic pain result in sudden acute inflammatory pain and do not mimic the prolonged normal tissue repair physiology which occurs after many human injuries. Perineural tissue changes can occur after an injury that leads to altered functioning of a nerve and to the ultimate development of pain-related behaviors. In this regards, none of the current models represent the gradual onset of neurogenic pain, since the neuropathic pain they represent is initiated with a very direct injurious method.

Furthermore, all current animal models involve some type of known nerve injury. Yet, the majority of persistent "non-malignant" pain treated by physicians has no known nerve injury as a cause, although the origin is attributed to being neurogenic or neuropathic. Persistent pain can develop as a response to often clinically, non-detectable tissue injury, not only as a response to direct trauma. After a soft tissue injury, there appears to be a functional disturbance of an associated nerve, which can lead to the demonstration of pain behavior. The cause or location of this disturbance, perturbation or ectopic firing on a nerve is not currently identified.

There is a long-standing need for an animal model representing patients with chronic pain without nerve damage. The need for an animal model for pain without clinical evidence of nerve injury has been recognized and preliminary attempts have been made. Reyna et al. (ICLAS, Palma de Malloren, May 26-28, page 226, 1999) developed an open surgical rat model for CRPS I that involved surgical placement by the tibial nerve of collagen. This surgical model produced pain responses characteristic of known neurogenic pain in the rats. For example, the responses were delayed in onset by about 14 days. The responses included sensitivity to light touch (mechanical allodynia), and persisted for up to 43 days. In addition, these animals exhibited an analgesic response to morphine sulfate and gabapentin. However, the creation of this animal model involved a surgical procedure to expose the posterior tibial nerve on one leg of the animal. The open surgical procedure could cause a certain degree of direct tissue injury. Thus, additional models for persistent neuropathic pain are needed, in particular, models that involve minimal tissue injury.

SUMMARY OF THE INVENTION

The present invention provides for the first time a non-surgical, non-traumatic non-human mammalian model for neurogenic pain of gradual onset lasting months. In contrast to models that are currently available in the art, the animals under the present study were walking normally within minutes of the procedure without evidence of immediate, acute pain or deformities and required no special care, which are similar to humans with chronic nonmalignant neural pain.

In particular, the present invention is directed to a method for producing a non-human mammalian model for neurogenic pain. This method comprises the step of altering a peripheral nerve of a non-human mammal by non-surgically placing a gel substance into the fascial tunnel through which the peripheral nerve passes. The placement of the gel substance leads to one or more pain behaviors, thereby producing a non-human mammalian model for neurogenic pain.

The present invention is also directed to a non-human mammalian model for neurogenic pain. In this mammalian model, a peripheral nerve in the mammal has been altered by non-surgically placing a gel substance into the fascial tunnel through which the peripheral nerve passes, wherein the placement of the gel substance leads to one or more pain behaviors.

The present invention is also directed to a method for screening a therapeutic agent for efficacy in treating neurogenic pain. This method comprises the steps of producing a non-human mammalian model for neurogenic pain according to the present invention; obtaining pain behavior of the mammalian model, wherein such pain behavior is pre-treatment pain behavior; administering a therapeutic agent to the mammalian model; and obtaining pain behavior of the mammalian model administered with the therapeutic agent, wherein such pain behavior is post-treatment pain behavior. An alteration identified as reduced mechanical allodynia, reduced mechanical hyperalgesia, or reduced mechanical allodynia and mechanical hyperalgesia in the post-treatment pain behavior as compared to the pre-treatment pain behavior is indicative of efficacy of the therapeutic agent in treating neurogenic pain.

The present invention is further directed to a method for screening a treatment for efficacy in treating neurogenic pain. This method comprises the steps of producing a non-human mammalian model for neurogenic pain according to the present invention; obtaining pain behavior of the mammalian model, wherein such pain behavior is pre-treatment pain behavior; conducting a treatment on the mammalian model; and obtaining pain behavior of the mammalian model after the treatment, wherein such pain behavior is post-treatment pain behavior. An alteration identified as reduced mechanical allodynia, reduced mechanical hyperalgesia, or reduced mechanical allodynia and mechanical hyperalgesia in the post-treatment pain behavior as compared to the pre-treatment pain behavior is indicative of efficacy of the treatment in treating neurogenic pain.

The present invention is still further directed to a method for screening an analgesic agent for analgesic effect in neurogenic pain. This method comprises the steps of producing a non-human mammalian model for neurogenic pain according to present invention; obtaining pain behavior of the mammalian model, wherein such pain behavior is pre-analgesic pain behavior; administering an analgesic agent to the mammalian model; and obtaining pain behavior of the mammalian model administered with the analgesic agent, wherein such pain behavior is post-analgesic pain behavior. An alteration identified as reduced mechanical allodynia, reduced mechanical hyperalgesia, or reduced mechanical allodynia and mechanical hyperalgesia in the post-analgesic pain behavior as compared to the pre-analgesic pain behavior is indicative of analgesic effect of the analgesic agent in neurogenic pain.

The present invention is still further directed to a composition effective for treating neuropathic pain. This composition comprises a therapeutically effective amount of a therapeutic agent identified by the method of the present invention and a therapeutically acceptable carrier.

DETAILED DESCRIPTION OF THE INVENTION

The present invention provides a method for creating a nonhuman mammalian model of persistent neurogenic pain with multiple variations of the model described. These variants were developed using various peripheral spinal nerves and spinal lumbar nerve roots with various gels placed in the fascial tunnels surrounding the nerves. The same non-traumatic, percutaneous, kinesthetic methods were used to create nerve alterations in these variants.

The present invention also provides a nonhuman mammalian model of persistent neurogenic pain with multiple variations of the model described. The variations of the biogenic neural pain model not only demonstrate pain behaviors of allodynia and hyperalgesia, but also respond to analgesics.

In particular, the present invention is directed to a method for producing a non-human mammalian model for neurogenic pain. This method comprises the step of altering a peripheral nerve of a non-human mammal by non-surgically placing a gel substance into the fascial tunnel through which the peripheral nerve passes. The placement of the gel substance leads to one or more pain behaviors, thereby producing a non-human mammalian model for neurogenic pain.

Preferably, the peripheral nerve can be a peripheral spinal nerve or a spinal lumbar nerve root. Representative examples of suitable peripheral spinal nerve include a tibial nerve, a peroneal nerve, a saphenous nerve and a sciatic nerve, whereas examples of the spinal lumbar nerve roots include lumbar nerve roots L4 and L5.

Still preferably, the gel substance can comprise collagen, hydrogel or both, and the one or more pain behaviors can include mechanical allodynia, mechanical hyperalgesia or both. Representative examples of mechanical allodynia include static mechanical allodynia, dynamic mechanical allodynia or both.

The present invention is also directed to a non-human mammalian model for neurogenic pain. In this mammalian model, a peripheral nerve in the mammal has been altered by non-surgically placing a gel substance into the fascial tunnel through which the peripheral nerve passes, wherein the placement of the gel substance leads to one or more pain behaviors.

Preferably, the peripheral nerve can be a peripheral spinal nerve or a spinal lumbar nerve root. Representative examples of suitable peripheral spinal nerve include a tibial nerve, a peroneal nerve, a saphenous nerve and a sciatic nerve, whereas examples of the spinal lumbar nerve roots include lumbar nerve roots L4 and L5.

Still preferably, the gel substance can comprise collagen, hydrogel or both, and the one or more pain behaviors can include mechanical allodynia, mechanical hyperalgesia or both. Representative examples of mechanical allodynia include static mechanical allodynia, dynamic mechanical allodynia or both.

The present invention is also directed to a method for screening a therapeutic agent for efficacy in treating neurogenic pain. This method comprises the steps of producing a non-human mammalian model for neurogenic pain according to the present invention; obtaining pain behavior of the mammalian model, wherein such pain behavior is pre-treatment pain behavior; administering a therapeutic agent to the mammalian model; and obtaining pain behavior of the mammalian model administered with the therapeutic agent, wherein such pain behavior is post-treatment pain behavior. An alteration identified as reduced mechanical allodynia, reduced mechanical hyperalgesia, or reduced mechanical allodynia and mechanical hyperalgesia in the post-treatment pain behavior as compared to the pre-treatment pain behavior is indicative of efficacy of the therapeutic agent in treating neurogenic pain.

The present invention is further directed to a method for screening a treatment for efficacy in treating neurogenic pain. This method comprises the steps of producing a non-human mammalian model for neurogenic pain according to the present invention; obtaining pain behavior of the mammalian model, wherein such pain behavior is pre-treatment pain behavior; conducting a treatment on the mammalian model; and obtaining pain behavior of the mammalian model after the treatment, wherein such pain behavior is post-treatment pain behavior. An alteration identified as reduced mechanical allodynia, reduced mechanical hyperalgesia, or reduced mechanical allodynia and mechanical hyperalgesia in the post-treatment pain behavior as compared to the pre-treatment pain behavior is indicative of efficacy of the treatment in treating neurogenic pain.

The present invention is still further directed to a method for screening an analgesic agent for analgesic effect in neurogenic pain. This method comprises the steps of producing a non-human mammalian model for neurogenic pain according to present invention; obtaining pain behavior of the mammalian model, wherein such pain behavior is pre-analgesic pain behavior; administering an analgesic agent to the mammalian model; and obtaining pain behavior of the mammalian model administered with the analgesic agent, wherein such pain behavior is post-analgesic pain behavior. An alteration identified as reduced mechanical allodynia, reduced mechanical hyperalgesia, or reduced mechanical allodynia and mechanical hyperalgesia in the post-analgesic pain behavior as compared to the pre-analgesic pain behavior is indicative of analgesic effect of the analgesic agent in neurogenic pain.

The present invention is still further directed to a composition effective for treating neuropathic pain. This composition comprises a therapeutically effective amount of a therapeutic agent identified by the method of the present invention and a therapeutically acceptable carrier. Preferably, the therapeutic agent is an analgesic agent.

In the context of the present invention, the term "peripheral nerve" is defined as all peripheral spinal nerves, all peripheral autonomic nerves and all spinal nerve roots. The terms "neurogenic pain" and "neuropathic pain" are defined based on Medline PLUS Mirriam Webster Medical Dictionary (2006) for the purpose of the present invention, with the term "neurogenic" being a more general term meaning "originating in nervous tissue; induced, controlled, or modified by nervous factors; disordered because of abnormally altered neural relations", whereas the term "neuropathic" being a more specific term meaning "an abnormal and usually degenerative state of the nervous system or nerves." Accordingly, neuropathic pain will be considered a subset of neurogenic pain in the context of the present invention.

In the context of the present invention, the term "non-traumatic" is defined as a method that does not cause acute pain or an acute immune reaction, or is not due to direct trauma to the nerves by methods that would include but not be limited to direct irritation, heating, freezing, cutting, crushing, or binding.

Also in the context of the present invention, the term "nondestructive" is defined as a condition whereby there are no observable signs or symptoms (such as paralysis, limping, weakness, erythema, cyanosis, or chewing behavior) of nerve injury and/or no observable pathological signs of nerve cell death or destruction (such as muscle atrophy, paralysis or foot deformity). Nondestructive nerve injury, however, may be associated with factors such as changes in regional limb temperatures, hypersensitivity to light touch, heat and/or cold, and possibly tremors or spasms.

Further in the context of the present invention, the term "nerve" refers to any type of nervous system tissue or cells, in vivo or in vitro, including whole nerve bundles, the spinal cord, the brain, the central nervous system, the autonomic nervous system, isolated nerve cells, neurons, and any type of cellular preparation that includes nervous system cells or associated tissue, including Schwann cells, glia cells and collagen matrix cells.

The present invention includes all neurogenic alterations to a nerve, including neuropathic alterations. In the context of the present invention, physiologic changes around a nerve would include alterations in any of the local hormones, growth factors, cytokines, or gene expression; many of these lead to pain responses or behaviors in an animal, including humans, as well as producing detectable changes in the physiology of the nerve at the site of alteration, where such changes can be detected by "in vivo" imaging methods such as radiography, bioluminescence, quantum dots, pet scans or functional MRI.

The focus of the present invention is production of a nondestructive, yet maintainable, alteration affecting a nerve. This may be accomplished by a variety of methods that would include but not be limited to placement of a biocompatible substance in proximity to the nerve, either directly or indirectly, surgical or non-surgical placement of the biocompatible substance, as well as use of transcutaneous, percutaneous or external forces to apply pressure on the nerve. In most instances, in order to produce a nondestructive and physiological alteration to a nerve, it is necessary to have the presence or creation of a biocompatible substance, which does not immediately produce any irritation or inflammatory response or any physiological response that would lead to an immunological reaction to the chosen substance in the body, as seen in acute pain. Such biocompatible substances would include but not be limited to collagen, fibrin, fibronectin, cellular extracts with other cells such as fibroblasts, the addition of stimulative cytokines, growth factors and/or hormones, elastin, autogenic extracts of stimulative cells, or any other biological or inert substance or substances that when administered either alone or in combination would directly or indirectly stimulate collagen production. Of particular interest are biocompatible substances in a viscous or colloidal form, herein referred to as gels, and those that have an elastic body that can produce an elastic deformation of the nerve cells, wherein an elastic deformation is defined as a change in the shape of the nerves. The biocompatible substance suitable for the present invention is capable of generating a mechanical force on the nerve in a nondestructive manner, wherein a nondestructive manner is defined as a manner wherein no discernable neurological deficit is observed in the live animal.

Since biocompatible substances with a wide variety of molecular structures, densities, and fluidities may be used in the present invention, the particular substance(s) chosen for use may vary. The factors to consider when choosing a biocompatible substance for use in the present invention include the ability of the substance not to induce an immune reaction or immediate inflammatory reaction within its immediate environment, as well as the nature of the substance which allows for direct or indirect production of a physiological nondestructive alteration or pressure on a nerve. Thus, the preferred substance must be both biocompatible and capable of producing or inducing nondestructive alterations and/or pressure on the nerve. Many polymers currently used in surgical and cosmetic procedures in humans and animals are biocompatible with rare immunogenic reactions and can be used in the creation of the neural alteration of the present invention. These substances would include but not be limited to any type of suture material, any hemostatic agent, or any material used in general, cardiothoracic, or plastic surgery of animals. Examples would include but not be limited to polyglycolic acid, colloids or suspensions with racemic forms of lactic acid, and emulsions with an oleaginous medium. Sclerosing agents such as formaldehyde and propylene glycol act by changing the nature of tissue in vivo by processes such as protein alteration or dehydration. These and similar processes can stimulate the tissue repair process with the production of collagen resulting. Any agents that can non-immunogenically alter or harden tissues in vivo ultimately resulting in fibrosis are suitable for the present invention.

The biocompatible substance used in the present invention can be any molecular/polymer complex capable of inducing physiologic alterations or pressure to a nerve through either direct or indirect reactions. The substances can include those that produce either immediate or delayed reactions. Therefore, the present invention could employ elastic biomaterials or solids or liquids which change their consistency at body temperature to provide an alteration by the nerve. Examples of such other substances would include but not be limited to: inflatable or deformable membranes, a gas reaction substance; a magnetic or electromagnetic gel; mutated or genetic variants and transgenic cells or organisms created to induce the desired alteration; expandable or collapsible mesh structures; electric, or magnetic methods with or without biochemical mechanisms or enzymes, and any mechanical device or method which creates an increase in neural physiologic pressure, temporarily or permanently, to include methods such as nanotechnology and bioengineering. Also useful would be substances that directly or indirectly increase the production of collagen or collagen-related changes in tissue, substances that would include fibrin, antibodies, antigens, fibroblasts, stimulating hormones, growth factors, and cytokines, among others.

The biocompatible substance used in the present invention is usually placed so as to surround or contact the chosen nerves. Particularly useful are substances which provide for a circumferential elastic force to be placed on the nerve. This substance does not have to surround or be in a circular position to produce such a circumferential force. Instead, the substance could produce a force area that is irregular in shape, due to the physical limitations of the surrounding tissues. The substance may directly or indirectly produce a compressive force or induce a physiological reaction to create a neural alteration.

Methods for delivery of the biocompatible substance to the site of production of the nondestructive compression injury in the present invention are non-traumatic and minimally invasive methods. In the context of the present invention, the term "non-surgical" is defined as a method that does not rely on an open surgical incision of the skin or any other tissue for open, visualized placement of a biocompatible substance. The biocompatible substance can be placed percutaneously by a skilled operator or by using indirect exploratory techniques that could utilize fiberoptics and/or endoscopy. In the context of the present invention, a skilled operator is a person or machine performing this method on a living organism with any device, tool or method that places the biocompatible substance by the identified nerve "non-surgically". These would include but not be limited to a needle and syringe. In a preferred embodiment, the placement device is a hypodermic needle with a 30 to 45 degree angle constructed with the needle bevel facing upwards. A skilled operator would choose the size and angle of the needle based on the animal to be used in the model for placement of the gel around the nerve. In the present study, needles of 23 gauge were used.

After the alteration or compression of the nerve has been produced, either by the method of the present invention or by nature (i.e., a naturally-induced nondestructive nerve alteration), the change in the local physiology of the nerve may be detected non-invasively. Neural alterations can result in changes or dysfunction related to processes that would include but not be limited to neural regeneration, neural edema, neural inflammation, mechanical pressure, blood flow and electrical conduction. All of these alterations can produce changes that can be detected or imaged by present and future methods. Therefore, also contemplated by the present invention are methods for developing detection or monitoring instruments, devices, or techniques for detection of the non-observable physiologic changes consequent to the development of neural alterations, such as temperature changes, alterations in electrical conductivity, or changes in substances produced by the nervous system or other bodily tissues or systems. These physiological changes may occur at the local area of neural alteration or occur elsewhere in the organism's body.

The present invention relates to a method for producing a nondestructive nerve alteration or compression in vivo in an animal that is a non-traumatic model for persistent neuropathic pain in humans. The model involves altering the local physiology or compressing a nerve in an animal so that an observable sign or physiologic change is detected, wherein that sign is indicative of persistent neurogenic pain. In one embodiment, the method for producing the nondestructive nerve alteration is due to injection of a collagen gel substance around a nerve. The clinical sign of neurogenic pain can be any form of spontaneous or elicited pain behavior, including mechanical allodynia (i.e., hypersensitivity to light touch). Therefore, the present invention relates to a non-traumatic animal model for persistent neurogenic pain wherein a biocompatible substance is placed near a nerve to induce an alteration or compression capable of causing pain behavior or causing the physiologic changes that occur in pain conditions. The present invention also relates to a method of detecting and monitoring persistent neurogenic pain in vivo wherein the physiological changes in the cell or organism that are indicative of a nerve compression or alteration associated with neurogenic pain are detected.

The present invention further includes methods for screening treatments for efficacy in treating persistent neurogenic pain comprising employing the animal model of the present invention and testing those animals for the presence of observable or physiological signs or evidence of nondestructive nerve compression or alteration associated with neurogenic pain both before and after a treatment. As a result, the present invention also relates to a method for developing treatments for persistent neurogenic pain in humans wherein the treatments are screened or developed by the method of the present invention.

The present invention further relates to a method for screening for substances that can be used to treat persistent neuropathic pain in animals, including humans. Substances under development for testing of analgesic activity, or any process or device useful for treatment of neuropathic pain, would be screened or developed through use of the animal model of the present invention. Behavioral or physiologic responses of the animals at baseline, before placement of the biocompatible substance, two to four weeks after placement, and then after administration of doses of the substance to be tested for analgesic activity would be determined. In the context of the present invention, behavioral and physiologic responses would include but not be limited to: 1) any observable behavior change such as reactions to heat, cold, vibration, pinprick, light, or light touch by any method; and 2) any non-observable but detectable physiologic reactions at the cellular level (i.e., changes in gene expression, growth factors, cytokines, enzymes, regeneration, cellular products, ion channels, adhesion properties, apoptosis, proteins levels, metabolism, signal transduction, pressure, receptor activity or numbers of receptors, cellular form, and/or anatomy) and at the molecular level (i.e., changes in function, action, mechanics, products, or ligands). These behavioral and/or physiological responses may occur as a result of changes in the nervous, circulatory, endocrine and/or lymph system of an animal, or due to changes in its supportive connective tissue. Reduction in pain responses after administration of the test substance as compared to the identified pain responses occurring after placement of the gel would indicate that the substance being tested is a candidate for treatment of humans. One of skill in the art would understand that the method of the present invention for screening new substances is one part of the drug development process for human therapeutics and would proceed with further development based on the results of the animal model testing of the present invention. Therefore, the present invention also includes a method for development of drugs or substances or devices or methods for treatment of neurogenic pain. The non-traumatic methods of the invention can lead to new cell and/or gene based drug screening techniques, such as high throughput drug screening assays, providing a powerful new approach to drug development. Thus, certain preferred results of this invention will be methods of pain diagnosis and pain treatments, identified by research and development techniques or products derived from the present invention.

Therefore, one of skill in the art would use this method of screening to develop treatments for nondestructive nerve injury. Techniques or treatments that are capable of relaxing or releasing a nerve compression, or changing the induced neural alterations, would be identified with the use of the animal models produced in the present invention. Therefore, the use of the method of the present invention would include screening for any substance or technique that alters the physiology of the neuron at the site of created alteration, with the consequent reduction of pain behaviors and/or resolution of associated physiological changes related to nondestructive nerve injury or inflammation. Treatments that could be tested using the method of the present invention would include all optic, facial, oral, intraperitoneal, fascial, intramuscular, intravenous, transcutaneous, subcutaneous, cutaneous, nasal, and/or rectal and vaginal or genital treatments.

Since the method of the present invention relates to a nondestructive and non-traumatic method, also contemplated by the present invention would be cellular or physiological simulation programs, including living cell systems, which model the physiology of neural networks that govern cell behavior. Therefore, the present invention would include any software program, cell screening assay or therapeutic screening with an "in vivo" multicellular system which simulates any of the neural alterations demonstrated in this invention. Since changes near a cell can affect biochemical processes of individual cell and cell group, any programs which simulate the reaction of a nerve or its environment to neural changes found in this model are included in the present invention.

Based on the knowledge that non-traumatic alterations and compression of a nerve can result in no obvious signs of nerve injury other than persistent pain, a method of detection of naturally-occurring neural alterations or compression was sought and discovered and then shown to be effective in humans. Evidence of neural compression in humans has been based on a clinical examination involving palpation for neural inflammation tenderness and/or dysesthesias (Tinel's signs). The physical or diagnostic examination can also be based on changes in electrophysiological parameters, clinical sensory testing, quantitative sensory analysis or biomechanical provocative testing. MRI imaging has also been used to visualize neuroanatomical structural changes. However, the use of MRI techniques to visualize the locations of neural compressions has been limited to changes in large nerve bundles and the central nervous system. The present invention provides a method for localizing altered neural physiology on peripheral nerves, especially small distal ones. The tool used to detect the changes is a receiver type device that amplifies electrical signals from neural tissue. In human patients with complaints of neurogenic pain, without a history or evidence of direct trauma or nerve transection, the device has detected distinctive electrical signal changes at or near the sites of neural alterations or compressions.

The following examples are included to demonstrate preferred embodiments of the invention. It should be appreciated by those of skill in the art that the techniques disclosed in the examples which follow represent techniques discovered by the inventors to perform reliably in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention. One of skill in the art will appreciate that certain embodiments of the invention provide methods of treating disease in humans and non-human mammals. These methods include all techniques common in the art for administering substances to mammals. It is within the skill of one in the art to optimize delivery techniques and dosages, depending on particular circumstances.

EXAMPLES

Example 1

Mouse Pain Model Demonstrating Mechanical Allodynia

Although rodent models were primarily used in the present study and discussed below in detail, the biocompatible substance and present method can be used in other types of animal models for generating physiological changes associated with persistent neuropathic pain. Other animals for models can include fish, amphibians, reptiles, birds, and mammals other than rodents, including humans. Induction of a neural alteration with application of a biocompatible substance near nerves can be demonstrated with various unicellular neurocytes, nerve cells or nerve nets of coelenterata, nerve cells including the giant axons of annelida, squid, and mollusca phylum among the invertebrates, as well as the neurons or related nerves of the peripheral, autonomic and central nervous system of vertebrates. The animal pain model of the present invention can be applied to all embryonics, clones, single nucleotide polymorphisms and transgenics of the cells and organisms mentioned above.

The animal model was produced based on the detection of pain behavior in rodents. Retired male breeder mice (5 AKR/J and 5 C57BL/6J) were housed singly. Baseline von Frey testing for pain behavior, in this case mechanical allodynia, was performed on three different days over a one week period and the results were averaged. In the method of von Frey testing for sensitivity to light touch, the plantar hind paw on the left leg was used for testing. At regular intervals, the response of the paw to light touch in terms of paw withdrawal was tested. Light touch was provided with a camel hair brush as well as two different von Frey fibers (4.13 and 4.73). All light touch stimuli (1 brush and 2 von Frey fibers) were touched to the left paw ten times each and the number of paw withdrawals was recorded and averaged for all stimulations. These stimulation tools are standard tools used in determining pain behavior to the normally non-painful stimulus of a light touch. The abnormal response to light touch is known as mechanical allodynia and is currently the most sought-after pain behavior in animal models of neuropathic and neurogenic pain.

Biocompatible collagen was prepared for use in the present study. The collagen source was dry gelatin that was prepared using sterile techniques. The dry collagen was measured to 2.5 grams and mixed with 7.5 cc of sterile normal saline. The mixture was heated for 30 seconds in a microwave on 80% power, The mixture was kept soft in warm water (approximately 100 to 110 degrees).

The consistency of the resulting warm collagen was such that it was able to pass through a 23 gauge needle. Humidity and other factors such as temperature can affect the consistency of the substance. 1-cc syringes were used for injection of 0.2 to 0.25 cc of collagen. For the injection, 23 gauge 1" standard luer lock hypodermic needles were used. The needles were very slightly dulled with a metal file at the tip and edges using sterile technique. The needles were angled at the midpoint with a bevel tip up. The angle was between 30 and 45 degrees, but any angle that allows for easy placement of the injected substance could be used. The needles were then attached to the collagen-filled one cc syringes. The syringes were kept in a warm water bath (100 to 110° F.) to maintain proper gel consistency.

The mice were lightly anesthetized with 1.5 to 2% isoflurane. The mice were then stabilized and aligned such that the left posterior leg was in view. The external anatomic landmarks of the posterior popliteal area were identified. The internal anatomy of this area including the posterior tibial nerve with its artery was mentally visualized with kinesthetic techniques. Kinesthetic techniques are methods that use the kinesthetic sense or the integration of the senses by which movement, mass, turgor, shape, resistance, elasticity, temperature, spatial relationships and position are commonly perceived. It also refers to the integrated use of multiple senses such as touch, proprioception, vision, and hearing. After location of the site for placement of the gel, the needle and syringe were then removed from the warm water bath. The distal portion of the needle was held loosely parallel to the tibia. The needle was allowed to gently penetrate through the dermis by pulling the skin taut over the popliteal fossa. With careful avoidance of tissue resistance, the needle tip, bevel up, was gently slipped beneath the fascial edge of the soleus muscle by the tibial nerve and artery into the deep posterior fascial compartment of the posterior tibial neurovascular tunnel, which is the neurovascular tunnel for the posterior tibial nerve and its proximal branches. When the tip of the needle was at the mid soleus muscle belly, the collagen mixture was slowly injected into the posterior tibial tunnel. The needle was removed and the animals allowed to recover from the anesthetic. All animals were normally moving freely within 20 minutes of anesthesia withdrawal.

Two days after placement of the collagen gel around the nerve, von Frey testing was again performed. Von Frey testing continued for 49 days. On day 49 post placement of the collagen, analgesic testing was initiated using intraperitoneal morphine sulfate (1 and 5 mg/kg IP) and gabapentin (25 and 40 mg/kg IP) with normal saline as a carrier and diluent. The results of the testing for mechanical allodynia are presented below in Table 1.

TABLE 1

Results of von Frey Testing in Mice with Neural Compression (n = 10)

| Day of Testing/Conditions | Average # Paw Withdrawals |
|---|---|
| Baseline testing | 3.59 |
| Post procedure day 2 | 2.78 |
| Post procedure day 7 | 2.37 |
| Post procedure day 9 | 4.29 |
| Post procedure day 14 | 6.22 |
| Post procedure day 23 | 5.67 |
| Post procedure day 30 | 8.08 |
| Post procedure day 42 | 8.75 |
| Post procedure day 49 | 8.71 |
| Plus morphine (1 mg/kg) | 8.71 |
| Post procedure day 51 | 8.88 |
| Plus morphine (5 mg/kg) | 6.66 |
| Post procedure day 58 | 9.14 |
| Plus gabapentin (25 mg/kg) | 6.86 |
| Post procedure day 65 | 9.19 |
| Plus gabapentin (40 mg/kg) | 5.81 |
| Post procedure day 73 | 9.24 |
| Post procedure day 79 | 9.48 |
| Post procedure day 86 | 8.67 |
| Post procedure day 107 | 8.33 |

The higher numbers correlate with an increase in the pain behavior of mechanical allodynia. All mice demonstrated mechanical allodynia within two to three weeks of placement of the collagen. Within 14 days, the differences in responses were statistically significant from baseline levels. The response continued for the entire period of the experiment or 107 days. Analgesic responses were shown when doses of morphine were at least 5 mg/kg IP and doses of gabapentin were either 25 or 40 mg/kg IP.

Example 2

Rat Pain Model Surgically Produced

Male rats (350 to 400 g) were housed singly. Over ten days four periods of baseline behavioral testing to mechanical light touch, pinprick, heat and cold applied to the plantar surface of the left hind paw were performed for control data. All testing was done in an open cage without restraints. In particular, light touch was tested with five von Frey fibers (3.61, 4.31, 4.74, 4.93 and 5.18) with ten stimulations of each fiber, 2 to 4 seconds apart in ascending order of pressure in each testing period. Pinprick was tested with a sharp, non-penetrating metal point adhered to a postage scale (point up) and gently pressed against each paw with a weight reading taken at time of paw withdrawal. This test was performed 6 times in each testing period. Heat and cold responses were tested with a large, peltier type floor thermode. The temperature was gradually raised (32 to 50° C.) to test heat responses and cold was tested by gradually lowering the temperature (32 to 5° C.). The temperature was then returned to 32° C. on ipsilateral hind paw withdrawal. The heat and cold stimulations were done 6 times each in separate sessions. Ipsilateral hind paw withdrawal was considered the positive endpoint in testing of all stimulation types noted.

After establishing baseline responses in each animal, the material for placement near the nerve was prepared. The preferred substance was sterile, purified Type I collagen (5 mg/ml) neutralized and mixed to a 5% sterile normal saline solution (pH 7.4). This mixture was kept under refrigeration and used while still cold as it can solidify at warmer temperatures. Humidity, pH, and temperature in the room can affect the consistency of the collagen. The consistency needs to be fluid enough for passage through a 23 gauge needle. A 0.2 cc sample of collagen was drawn into a cold 1 cc syringe with a 23 gauge one inch hypodermic needle and then refrigerated.

The animals to be injected were lightly anesthetized and shaved at the left medial thigh. An open, transcutaneous skin incision was made over the middle of the medial thigh and the left saphenous nerve and artery were exposed and visualized with operating microscope. The cold collagen was injected around the saphenous nerve after gently coercing the needle through the neurovascular fascia with the needle bevel face up between the saphenous nerve and artery. The saphenous nerve should be over the bevel with the artery posterior to the needle tip. The collagen mixture was then extruded through the needle bevel until it was seen through an operating microscope to encircle the saphenous nerve in the neurovascular fascia. The entire 0.2 cc of collagen mixture may not need to be used. After collagen placement, visualization of the artery was done to ensure that a clear arterial pulse was present, without visible bleeding. The needle was withdrawn through the same hole in the fascia that was made on entry. The skin incision was closed with nylon sutures.

All rats were allowed to move freely within 20 minutes of surgery. There were no visible signs of edema, cyanosis, ecchymoses, or guarded gait after surgery, or at any later time. The ipsilateral plantar hind paws at the midfoot area were then tested biweekly for responses to light touch, pinprick, heat and cold as described above.

Example 3

Reversal of Mechanical Allodynia in a Mouse Model of Neurogenic Pain

Mice were prepared as described above by injecting collagen gel around the left posterior tibial nerve. All mice exhibited signs of neurogenic pain as determined by a mechanical allodynia response. After 79 days, six mice were selected for treatment with a mixture of a steroid (methyl-prednisolone 40 mg/ml) and 2% lidocaine as a way to reverse the neurogenic pain response. The mice were lightly anesthetized as before and then 0.2 cc of a solution of 10% methyl-prednisolone and 90% lidocaine was injected by the left posterior tibial nerve via the posterior tibial tunnel as previously described; this was the same nerve where the collagen had been placed.

The animals were then again tested for mechanical allodynia as characterized by the number of paw withdrawals to light touch. The results were indicative of a reversal of the mechanical allodynia in four of the six mice tested. Two mice had continued pain responses to light touch up to day 118, with an average number of paw withdrawals of between 9 and 10 (ten is the total number of positive paw withdrawals possible). Four mice, however, had an average number of paw withdrawals at day 118 of 3.1, a value that was near the level of their own baseline averages (3.4) and that was significantly lower than was seen in these same animals before treatment (an average of 9.2 total stimulations). These data demonstrate that the mixture of steroid and lidocaine was able to reverse the signs of neurogenic pain in this animal model. Thus, based on the results of testing in this animal model, the mixture of a glucosteriod and/or an anesthetic would be a potential therapy for treatment of a nerve alteration or compression and associated pain.

Example 4

Guinea Pig Model for Neurogenic Pain

In order to extend the model to species other than rats and mice, four guinea pigs were subjected to the saphenous vein procedure as detailed above in rats using a purified collagen material. Avitene, an absorbable, sterile, non-pyrogenic microfibrillar collagen hemostat was the form of collagen used. Avitene (71 mg) was mixed with 1.5 cc normal saline to a viscous consistency. The mixture was then heated in a microwave for approximately 30 seconds at 80% power, in a porous ceramic bowl. This mixture was then injected near the saphenous nerve as described above in rats. After placement of the collagen colloid, the guinea pigs were observed and tested for their response to pinprick. All guinea pigs had a significant difference in pinprick tolerance after placement of the collagen as compared to their baseline measurements before collagen placement. The ipsilateral leg to the saphenous nerve procedure exhibited a lower weight pressure limit to pinprick, i.e., it was more sensitive to the pinprick, than the contra lateral leg when the animals were tested between days 24 to 35 post-surgery. This pinprick testing in the guinea pig demonstrated another pain behavior, known as mechanical hyperalgesia, or a lower tolerance than normal to a normally painful stimulus.

Example 5

Other Variants of the Neurogenic Pain Model in Rats Demonstrating Mechanical Allodynia and Mechanical Hyperalgesia The methods of preparation and testing were similar for all the variant pain models described in this example. Male Sprague Dawley rats initially weighing between 150 and 175 grams were housed singly. Baseline behaviors to stimulations of the paw on which the procedure was to be performed were recorded over several sessions after accommodation of 3-4 days, and the results were averaged and used as the baseline control data. The pain behaviors studied were static mechanical allodynia (e.g., light touch stimulation with von Frey fibers 4.56, 4.73, 4.93, and/or 5.07), dynamic mechanical allodynia (e.g., stimulation with moving camel hair brush), and/or mechanical hyperalgesia (e.g., pinprick stimulation).

After the baseline control data was collected, the specified procedure with a gel was performed near the chosen nerve of each variant group (see Tables 2-6 and 8-10), then the rats were tested post procedurally and intermittently for up to 77 days for behavioral changes (see Tables 2-6 and 8-11) and for their responses to substances with analgesic properties (see Tables 7 and 12).

The stimuli used to elicit pain behavior were the von Frey fibers, camel hair brush and pinprick, with 6 stimulations of each stimulus. Each variant pain model had the same sequence of stimuli with the positive responses averaged and a student T-test performed for the significance of the post procedural responses as compared to the baseline control data (see Tables 2-6 and 11); and for the post-analgesic responses as compared to the pre-analgesic behavioral data (see Tables 7 and 12).

To ensure proper placement of the gel by the chosen peripheral nerve, three steps of preparatory examinations were performed for the variant models in this example. First, rat cadavers (in formalin) were dissected to study the anatomy of each nerve and its surrounding landmarks to help in conceptualizing the closed kinesthetic method as described in the previous examples. Second, the cadaver studies were then followed by trials of practicing the closed nonsurgical kinesthetic technique in "fresh" whole rats with a marker gel. These studies were performed within 20 minutes of euthanization to enable "in vivo" tissue qualities. The simulated nonsurgical placement of a marker gel (blue ink in a viscous gelatin) identified the best anatomic tunnels for the chosen nerves. The amount of marker used was 0.1 cc to 0.25 cc administered through a 23 gauge angled thin walled needle. Third, after a trial of simulated marker placement, immediate dissection was performed to confirm proper position of the marker gel in an identified neural tunnel. The blue marker gelatin was injected with the same kinesthetic percutaneous method as defined and described below for each specific peripheral spinal nerve or spinal nerve root.

The tunnels identified by the above studies were then used for the placement of the biocompatible gels by the chosen peripheral nerves. The gelatinous or viscous substances (i.e., the gels) placed by the peripheral nerves or nerve roots contained collagen (e.g., AVITENE® and gelatin) or hydrogels. The "collagen gel" used in the present study was composed of 0.8 grams of collagen as AVITENE® (microfibrillar collagen hemostat flour, Davol Inc., Cranston, R.I. 02920) and 0.7 grams of collagen as gelatin (Knox gelatin, Kraft Foods, Northfield, Ill. 60093) mixed with 14 cc of normal saline until homogenous. Then the collagen mixture was placed in a PYREX® bowl resting in a paper bowl and covered with a ceramic saucer, then heated for 20 seconds at full power in a microwave. The resulting viscous mixture was kept fluid in a warm water bath at 100-110° F., until used for the placement procedure. The wound hydrogels used in the present study were two types: one contains alginate (SAF-Gel® from ConvaTec of E. R. Squibb & Sons, Princeton, N.J.) and the other contains acemannan from Aloe vera L. (Carrasyn®V from Carrington Laboratories, Irving, Tex.). These hydrogels are considered non-immunogenic as such they are not irritating and do not elicit a significant immune response. Such hydrogels are used in the care of open dermal wounds as well as in first and second degree burns since they provide a closed moist environment for wound healing.

The rats were anesthetized with 1.5% to 2% isoflurane for the percutaneous kinesthetic placement of the above "gels" by the specified nerves. Using an angled 23 gauge thin wall 1" needle, approximately 0.1 cc-0.2 cc of gel was placed percutaneously with kinesthetic technique in the anatomically defined fascial tunnels of the chosen peripheral nerves as described below.

The gel placement in the "posterior" tibial nerve tunnel was previously described in earlier examples and again used in generating animal pain model variant in this example. The common peroneal nerve winds around the neck of the fibula and passes deep to the peroneus longus where it bifurcates forming the superficial peroneal nerve and deep peroneal nerve. In this peroneal nerve variant of the pain model, the chosen gel was placed within the anatomic fascial tunnel starting just beyond the bifurcation of the common peroneal nerve near the superficial peroneal nerve branch passing between the peroneus longus and peroneus brevis, then extending beside the lateral aspect of the extensor digitorum longum tendon.

The anatomic tunnel for the saphenous nerve is accessed in the lower medial thigh as it passes through an anatomic tunnel that is anatomically referred to as the "adductor canal". Just proximal to the canal the saphenous nerve lies beneath the satorius muscle, by the medial edge of the vastus medialis and medially just superior to the adductus longus and adductor magnus, and then passes over the femoral artery as it passes under the fascial vasoadductor membrane of the "adductor canal". When generating saphenous nerve variant of the pain model, the fascial tunnel of the saphenous nerve was entered percutaneously just proximal to the canal for gel placement within the canal.

The fascial tunnel of the sciatic nerve was entered percutaneously midway between the greater trochanter and the ischium with the rat lying on its side. The needle was directed distally beneath the piriformis and over the gemelli and obturator internus, and then over the quadratus femoris and adductor magnus. At midthigh the sciatic nerve was crossed obliquely by the long head of the biceps femoris. In this variant pain model, the gel was placed by the sciatic nerve in its fascial anatomic tunnel near the proximal midthigh region.

The fascial tunnel surrounding the lumbar 4 (L4) and lumbar 5 (L5) nerve roots lateral to the vertebral neuroforaminae was entered using the landmarks of the iliac crest and the prominent L5 vertebral spine. By percutaneously entering about 1 cm to 1.5 cm distally midway between these landmarks in a medial cephalic direction, the needle followed the muscular fascial tunnel of the lumbosacral trunk beneath the psoas major and over the quadratus lumborum to the paravertebral space near the L4 and L5 nerve roots, just lateral to their neuroforaminae. In this variant pain model, the gel was deposited near the end of the fascial tunnel close to the L4 and L5 spinal nerve roots.

Drugs known to have some analgesic value, particularly in neurogenic pain, were chosen to demonstrate their analgesic effect in these pain model variants. The doses were given intraperitoneally (I.P.) and behavioral stimulus testing began 40-80 minutes after the dose. The student's t-test (p<0.05) was performed for determining the significance of changes in behaviors associated with pain after the analgesic was administered.

The tables below provide data sets for the pain model variants described above. Each table depicts the number ("n") of rats, the chosen peripheral nerve site, the type of gel used, the pain behaviors studied at a certain number of days post procedure ("PostD") with average number of positive stimulations (AVE:) and p-values of the student T-test, as well as the response to the indicated doses of analgesics at a certain number of days post procedure.

TABLE 2

Tibial Nerve with Alginate Hydrogel (n = 5)

| | PinPrick w/ 6 stimulations | |
|---|---|---|
| TIME of TEST: | AVG: | T-test (p=): |
| Baseline of 4 days | 1.95 | NA |
| PostD 2 | 1.80 | 7.9E−01 |
| PostD 5 | 2.40 | 1.7E−01 |
| PostD 10 | 5.00 | 1.0E−03 |
| PostD 14 | 3.80 | 1.5E−05 |
| PostD 17 | 4.80 | 4.5E−04 |
| PostD 24 | 4.80 | 4.5E−04 |

TABLE 2-continued

Tibial Nerve with Alginate Hydrogel (n = 5)

| | PinPrick w/ 6 stimulations | |
|---|---|---|
| TIME of TEST: | AVG: | T-test (p=): |
| PostD 25 | 4.80 | 2.5E−03 |
| PostD 33 | 4.60 | 9.2E−03 |
| PostD 45 | 5.20 | 2.2E−03 |
| PostD 52 | 5.40 | 2.6E−03 |
| PostD 61 | 5.80 | 4.2E−09 |
| PostD 77 | 5.80 | 5.3E−10 |

TABLE 3

Tibial Nerve with Acemannan Hydrogel (n = 5)

| | von Frey 4.93 w/ 6 stimulations | | PinPrick w/ 6 stimulations | |
|---|---|---|---|---|
| TIME of TEST: | AVG: | T-test (p=): | AVG: | T-test (p=): |
| Baseline of 4 days | 0.30 | NA | 1.40 | NA |
| PostD 2 | 0.40 | 8.2E−01 | 1.80 | 3.7E−01 |
| PostD 5 | 0.40 | 7.2E−01 | 2.20 | 1.0E−01 |
| PostD 10 | 2.40 | 1.0E−02 | 4.00 | 6.6E−03 |
| PostD 14 | 2.80 | 1.9E−02 | 4.40 | 9.6E−03 |
| PostD 17 | 2.40 | 5.1E−03 | 4.80 | 1.2E−02 |
| PostD 24 | 3.20 | 3.5E−03 | 4.60 | 1.9E−03 |
| PostD 33 | 3.20 | 1.6E−02 | 4.60 | 1.9E−03 |
| PostD 45 | 3.40 | 5.2E−05 | 5.40 | 1.2E−04 |

TABLE 4

Saphenous Nerve with Collagen Gel (n = 4)

| | von Frey 4.93 w/ stimulations | | PinPrick w/ stimulations | |
|---|---|---|---|---|
| TIME of TESTS: | AVG: | T-test (p=): | AVG: | T-test (p=): |
| Baseline of 4 days | 1.03 | NA | 2.47 | NA |
| PostD 2 | 1.00 | 9.5E−01 | 3.25 | 4.1E−02 |
| PostD 5 | 1.00 | 9.8E−01 | 3.25 | 2.0E−01 |
| PostD 10 | 2.75 | 1.4E−01 | 4.50 | 4.6E−02 |
| PostD 14 | 3.75 | 1.3E−01 | 4.50 | 4.6E−02 |
| PostD 17 | 2.75 | 2.2E−01 | 4.25 | 6.0E−02 |
| PostD 24 | 3.00 | 1.7E−01 | 5.00 | 3.3E−02 |
| PostD 33 | 4.00 | 4.4E−02 | 5.50 | 1.0E−04 |
| PostD 45 | 3.00 | 1.2E−01 | 4.50 | 9.7E−04 |
| PostD 52 | 3.75 | 5.3E−03 | 5.25 | 5.7E−03 |
| PostD 61 | 3.75 | 5.3E−03 | 5.50 | 1.0E−04 |

TABLE 5

Peroneal Nerve with Collagen Gel (n = 5)

| | von Frey 4.93 w/ stimulations | | PinPrick w/ stimulations | |
|---|---|---|---|---|
| TIME of TEST: | AVG: | T-test (p=): | AVG: | T-test (p=): |
| Baseline of 4 days | 0.98 | NA | 2.33 | NA |
| PostD 2 | 1.20 | 6.7E−01 | 1.40 | 2.9E−01 |
| PostD 5 | 1.80 | 9.1E−01 | 3.40 | 1.9E−01 |
| PostD 10 | 3.80 | 9.5E−04 | 4.60 | 2.6E−01 |
| PostD 14 | 3.60 | 5.6E−03 | 5.40 | 4.8E−04 |
| PostD 17 | 3.20 | 9.0E−03 | 4.60 | 8.2E−03 |
| PostD 24 | 3.80 | 5.3E−06 | 5.60 | 1.4E−06 |
| PostD 33 | 4.00 | 7.9E−03 | 5.40 | 4.8E−04 |

TABLE 5-continued

Peroneal Nerve with Collagen Gel (n = 5)

| TIME of TEST: | von Frey 4.93 w/ stimulations | | PinPrick w/ stimulations | |
|---|---|---|---|---|
| | AVG: | T-test (p=): | AVG: | T-test (p=): |
| PostD 45 | 4.00 | 1.8E−03 | 5.00 | 1.1E−02 |
| PostD 52 | 4.20 | 4.4E−02 | 6.00 | 4.3E−22 |
| PostD 61 | 3.40 | 3.9E−02 | 5.80 | 1.3E−08 |

TABLE 6

Sciatic Nerve with Alginate Hydrogel (n = 4)

| TIME of TEST: | von Frey 4.93 w/ stimulations | | PinPrick w/ stimulations | |
|---|---|---|---|---|
| | AVG: | T-test (p=): | AVG: | T-test (p=): |
| Baseline of 4 days | 0.59 | NA | 2.22 | NA |
| PostD 2 | 1.20 | 6.7E−01 | 2.25 | 9.7E−01 |
| PostD 5 | 1.80 | 9.1E−02 | 2.50 | 4.4E−01 |
| PostD 10 | 3.80 | 9.5E−04 | 4.50 | 3.4E−02 |
| PostD 14 | 3.60 | 5.6E−03 | 4.50 | 9.5E−02 |
| PostD 17 | 3.20 | 8.9E−03 | 5.50 | 1.1E−04 |
| PostD 24 | 3.80 | 5.3E−06 | 5.50 | 1.1E−04 |
| PostD 33 | 4.00 | 7.9E−03 | 5.75 | 1.6E−05 |
| PostD 45 | 4.00 | 1.8E−03 | 5.50 | 4.2E−03 |
| PostD 52 | 4.20 | 4.3E−02 | 5.75 | 1.6E−05 |
| PostD 61 | 3.40 | 3.9E−04 | 5.50 | 1.2E−04 |

TABLE 8

Tibial Nerve with Collagen Gel (n = 4)
Average of Positive stimulations out of 6 total

| Time of Test | Stim A vF 4.56 Avg: | Stim B vF 4.93 Avg: | Stim C vF 5.07 Avg: | Stim S Camel Brush Avg: | Stim PP Pin Prick Avg: |
|---|---|---|---|---|---|
| Baseline of 4 days | 0.125 | 0.19 | 1.25 | 1.5 | 2.38 |
| PostD 2 | 0.0 | 0.0 | 0.25 | 0.0 | 1.5 |
| PostD 5 | 0.25 | 0.25 | 0.0 | 0.25 | 1.75 |
| PostD 12 | 0.0 | 0.25 | 0.75 | 0.0 | 2.0 |
| PostD 17 | 0.75 | 0.5 | 2.25 | 0.5 | 2.75 |
| PostD 25 | 0.5 | 1.75 | 3.0 | 2.0 | 4.5 |
| PostD 31 | 2.0 | 2.5 | 4.25 | 4.0 | 5.0 |
| PostD 36 | 1.75 | 2.5 | 2.0 | 3.25 | 4.0 |
| PostD 41 | 2.0 | 3.0 | 3.0 | 4.75 | 5.5 |
| PostD 58 | 2.25 | 3.0 | 3.0 | 4.25 | 5.0 |
| PostD 69 | 2.25 | 3.5 | 3.5 | 4.25 | 6.0 |

TABLE 9

Peroneal Nerve with Alginate Hydrogel (n = 4)
Average of Positive stimulations out of 6 total

| Time of Test | Stim A vF 4.56 Avg: | Stim B vF 4.93 Avg: | Stim C vF 5.07 Avg: | Stim S Camel Brush Avg: | Stim PP Pin Prick Avg: |
|---|---|---|---|---|---|
| Baseline of 4 days | 0.125 | 0.188 | 1.375 | 0.92 | 2.63 |
| PostD 2 | 0.0 | 0.0 | 0.25 | 0.0 | 1.0 |

TABLE 7

Analgesic Effects of Different Types of Analgesics on Pain Model Variants
(Total number of stimulations for each stimulus is 6;
*Carrier/diluent for tested analgesics was normal saline.)

| Student T-test P < 0.5 (5.0E−2) TYPE of RAT ("n." refers to nerve): | ANALGESIC*: | von Frey F 4.93 # STIMULATIONS | | Pinprick # STIMULATIONS | |
|---|---|---|---|---|---|
| | | PRE-ANALGESIC | POST-ANALGESIC | PRE-ANALGESIC | POST-ANALGESIC |
| 1 rat with tibial n. with Alginate hydrogel | Ketorolac 10% 0.1 cc IP | 6 | 6 | 6 | 6 |
| 1 rat with tibial n. with Acemannan hydrogel | Ketorolac 10% 0.1 cc IP | 6 | 5 | 6 | 6 |
| 1 rat with peroneal n. with Avitene collagen | Ketorolac 10% 0.1 cc IP | 6 | 6 | 6 | 6 |
| 1 rat with sciatic n. with Alginate hydrogel | Ketorolac 10% 0.1 cc IP | 5 | 2 | 6 | 5 |
| 1 rat with sciatic n. with Alginate hydrogel | Ketorolac 10% 0.1 cc IP | 6 | 3 | 6 | 6 |
| | Total: | 29 | 22 | 30 | 29 |
| | Pre- vs Post- T test, p=: | | 1.6E−1 | | 3.7E−1 |
| 1 rat with tibial n. with Alginate hydrogel | Morphine 5 mg/kg IP | 6 | 3 | 6 | 3 |
| 1 rat with tibial n. with Acemannan hydrogel | Morphine 5 mg/kg IP | 6 | 2 | 6 | 2 |
| 1 rat with peroneal n. with Avitene collagen | Morphine 5 mg/kg IP | 5 | 3 | 6 | 1 |
| 1 rat with sciatic n. with Alginate hydrogel | Morphine 5 mg/kg IP | 4 | 3 | 6 | 2 |
| 1 rat with sciatic n. with Alginate hydrogel | Morphine 5 mg/kg IP | 6 | 4 | 6 | 4 |
| | Total: | 27 | 15 | 30 | 12 |
| | Pre- vs Post- T test, p=: | | 1.8E−3 | | 2.1E−3 |
| 1 rat with tibial n. with Alginate hydrogel | Ethosuximide 100 mg/kg IP | 6 | 0 | 6 | 2 |
| 1 rat with tibial n. with Acemann hydrogel | Ethosuximide 100 mg/kg IP | 6 | 0 | 6 | 0 |
| 1 rat with saphenous n. with Avitene collagen | Ethosuximide 100 mg/kg IP | 4 | 0 | 6 | 1 |
| 1 rat with sciatic n. with Alginate hydrogel | Ethosuximide 100 mg/kg IP | 3 | 0 | 6 | 0 |
| 1 rat with sciatic n. with Alginate hydrogel | Ethosuximide 100 mg/kg IP | 6 | 0 | 6 | 1 |
| | Total: | 25 | 0 | 30 | 4 |
| | Pre- vs Post- T test, p=: | | 1.43E−3 | | 1.6E−4 |

TABLE 9-continued

Peroneal Nerve with Alginate Hydrogel (n = 4)
Average of Positive stimulations out of 6 total

| Time of Test | Stim A vF 4.56 Avg: | Stim B vF 4.93 Avg: | Stim C vF 5.07 Avg: | Stim S Camel Brush Avg: | Stim PP Pin Prick Avg: |
|---|---|---|---|---|---|
| PostD 5 | 0.0 | 0.25 | 0.25 | 0.5 | 1.5 |
| PostD 12 | 0.0 | 0.0 | 0.5 | 0.25 | 2.75 |
| PostD 17 | 1.0 | 0.75 | 1.75 | 1.75 | 3.25 |
| PostD 25 | 1.25 | 1.75 | 2.25 | 2.5 | 5.25 |
| PostD 31 | 1.0 | 2.5 | 4.0 | 3.75 | 5.5 |
| PostD 36 | 2.25 | 2.25 | 2.0 | 3.0 | 5.75 |
| PostD 41 | 2.25 | 3.25 | 3.25 | 4.75 | 5.75 |
| PostD 58 | 4.0 | 3.5 | 3.0 | 5.0 | 5.75 |
| PostD 69 | 2.75 | 3.25 | 2.75 | 3.5 | 5.25 |

TABLE 10

Lumbar 4 (L4) and Lumbar 5 (L5) Nerve Roots (*n = 4)
3 with Collagen Gel and 1 with Alginate Hydrogel Average of
Positive Stimulations out of 6 total for Each Stimulus

| Time of Test | Stim A vF 4.56 Avg: | Stim B vF 4.93 Avg: | Stim C vF 5.07 Avg: | Stim S Camel Brush Avg: | Stim PP Pin Prick Avg: |
|---|---|---|---|---|---|
| Baseline of 4 days | 0.5 | 0.875 | 2.06 | 1.33 | 2.94 |
| PostD 2 | 0.25 | 0.0 | 0.0 | 0.0 | 2.5 |
| PostD 5 | 0.25 | 0.25 | 0.75 | 0.5 | 2.5 |
| PostD 12 | 1.5 | 1.75 | 2.0 | 0.75 | 3.5 |
| PostD 17 | 1.0 | 1.75 | 2.25 | 1.75 | 3.75 |
| PostD 25 | 2.25 | 3.0 | 3.25 | 3.5 | 5.5 |
| PostD 31 | 2.5 | 3.75 | 3.5 | 4.75 | 5.25 |
| PostD 36 | 2.0 | 3.0 | 3.25 | 3.5 | 5.5 |
| PostD 41 | 4.25 | 3.75 | 3.75 | 4.75 | 5.75 |
| PostD 58 | 3.75 | 4.5 | 3.5 | 4.75 | 5.5 |
| PostD 69 | 3.0 | 3.25 | 3.5 | 5.25 | 5.5 |

TABLE 11

All rats in Tables 8-10 with significance ($p < 0.05$ or $< 5.0E-2$)
Student T-test (n = 12) Average (Avg) Positive Stimulations out
of 6 total w/Significance (p) as Compared to Baseline Average

| | Stim A vF 4.56 | | Stim B vF 4.93 | | Stim C vF 5.07 | | Stim S Camel Brush | | Stim PP Pin Prick | |
|---|---|---|---|---|---|---|---|---|---|---|
| Time of Test | Avg: | p= | Avg: | p= | Avg: | p= | Avg: | p= | Avg: | p= |
| Baseline of 4 days | 0.25 | — | 0.42 | — | 1.56 | — | 1.25 | — | 2.65 | — |
| PostD 2 | 0.83 | 1.5E−1 | 0.0 | 9.9E−5 | 0.17 | 9.8E−10 | 0.0 | 1.5E−8 | 1.67 | 6.8E−3 |
| PostD 5 | 0.17 | 8.2E−1 | 0.25 | 5.6E−1 | 0.3 | 3.5E−3 | 0.42 | 3.7E−3 | 1.92 | 2.2E−2 |
| PostD 12 | 0.5 | 4.8E−1 | 0.67 | 4.8E−1 | 1.08 | 2.6E−1 | 0.42 | 3.8E−3 | 2.75 | 8.2E−1 |
| PostD 17 | 0.92 | 9.2E−4 | 1.00 | 8.8E−2 | 2.08 | 2.8E−1 | 1.33 | 8.5E−1 | 3.25 | 1.5E−1 |
| PostD 25 | 1.33 | 7.9E−3 | 2.17 | 4.4E−3 | 2.83 | 1.1E−2 | 2.67 | 4.9E−3 | 5.08 | 1.4E−8 |
| PostD 31 | 1.83 | 7.3E−4 | 2.92 | 4.7E−5 | 3.92 | 2.4E−3 | 4.17 | 1.2E−4 | 5.25 | 2.8E−8 |
| PostD 36 | 2.00 | 9.7E−5 | 2.58 | 3.4E−5 | 2.42 | 2.5E−2 | 3.25 | 6.2E−4 | 5.08 | 7.0E−6 |
| PostD 41 | 2.83 | 1.4E−4 | 3.30 | 1.3E−6 | 3.33 | 1.9E−4 | 4.75 | 1.6E−12 | 5.67 | 1.6E−12 |
| PostD 58 | 3.33 | 4.6E−5 | 3.58 | 7.9E−6 | 3.25 | 6.7E−8 | 4.83 | 3.5E−10 | 5.50 | 1.1E−9 |
| PostD 69 | 2.67 | 1.5E−4 | 3.33 | 5.6E−6 | 3.25 | 1.7E−3 | 4.33 | 1.5E−5 | 5.58 | 6.5E−12 |

TABLE 12

Effects of Analgesics with All Rats in Tables 8-10 (n = 12)
Pre Stimulation Avg w/Post Stimulation Avg with Significance
($p < 0.05$ or $< 5.0E-2$) Student T-test Avg is Average Positive
stimulations out of 6 total w/Significance (p) as Compared to
Pre-Analgesic Average

| | Ethosuximide* 200 mg/kg (IP) | | | Gabapentin* 50 mg/kg (IP) | | | Morphine Sulfate* 5 mg/kg (IP) | | |
|---|---|---|---|---|---|---|---|---|---|
| STIM TYPE: | Pre Avg | Post Avg | p= | Pre Avg | Post Avg | p= | Pre Avg | Post Avg | p= |
| Stim A vF 4.56 | 1.83 | 0.5 | 2.9E−3 | 2.0 | 0.25 | 8.5E−5 | 2.83 | 0.33 | 1.6E−4 |
| Stim B vF 4.93 | 2.92 | 0.58 | 8.4E−5 | 2.58 | 0.5 | 5.8E−5 | 3.33 | 0.58 | 1.3E−6 |
| Stim C vF 5.07 | 3.92 | 0.83 | 1.4E−5 | 2.42 | 0.75 | 4.4E−4 | 3.33 | 0.83 | 6.1E−6 |
| Stim S Brush | 4.17 | 1.17 | 1.1E−4 | 3.25 | 1.25 | 9.5E−4 | 4.75 | 1.69 | 1.5E−6 |
| Stim PP Pin Prick | 5.25 | 1.75 | 1.4E−8 | 5.08 | 2.25 | 2.6E−5 | 5.67 | 2.17 | 2.0E−10 |

*Carrier/diluent for tested analgesics was normal saline.

CONCLUSION

The results of the use of various types of gels on various types of peripheral spinal nerves from the above tables demonstrate the similar effect of the gradual induction of recognized allodynic and hyperalgesic pain behaviors in all the variant models. As demonstrated in Tables 2-6, the majority of the models had the onset of significant pain behaviors by day 10 post procedure (i.e., PostD 10). The pain model with the gel injection placed by a saphenous nerve (see Table 4) had onset of significant allodynia for von Frey fiber 4.93 by day 33 (i.e., PostD 33), while hyperalgesia for pinprick starts on day 10 (i.e., PostD 10).

The analgesic testing presented in Table 7 shows that the nonsteroidal anti-inflammatory drug (NSAID) ketorolac had no significant analgesic effect. This lack of significant analgesia for ketorolac was clinically recognized in human patients with regard to neurogenic pain. Morphine at a high dose of 5 mg/kg IP had significant analgesic effect in the models, as has a moderate dose of Gabapentin at 50 mg/kg IP. See Tables 7 and 12.

The data in Tables 8-10 presents the gradual onset of allodynia in all four stimulations (von Frey fibers: vF 4.56, vF 4.93, vF 5.07, Camel Brush) and in hyperalgesia (Pin-Prick) in 3 distinct groups of variants of this rodent biogenic pain model. The pattern of gradual onset of pain behaviors was similar in all three groups, despite the different gels and various peripheral spinal nerves or lumbar nerve roots being used. The data presented in Table 11 combines the pain behaviors of different pain models of Tables 8-10 with their specific types of stimulation responses (i.e., von Frey fibers A: vF 4.56, B: vF 4.93, C: vF 5.07, S: Camel hair brush, and PP: PinPrick). By day 25 post procedure (i.e., PostD 25) the behavioral responses demonstrated significance for the indicated pain behaviors.

As demonstrated in Table 12, all chosen analgesics of ethosuximide, gabapentin and morphine Sulfate had significant analgesic effects on the rat groups from Tables 8-10 at the doses administered within 40-80 minutes. The analgesic effect on all variant rodent models is consistent with the response of neuropathic and neurogenic pain patients, that is, ethosuximide, gabapentin and morphine have a significant analgesic effect, whereas the prior mentioned ketorolac has no significant analgesic properties.

The data presented in this study support the hypothesis that biocompatible gels placed in the anatomic fascial tunnels of peripheral spinal nerves or lumbar nerve roots in mammals can cause the gradual biogenic induction of allodynic and hyperalgesic pain behaviors over several weeks to months. These behavioral changes may relate to the alteration of the perineural extracellular matrix (ECM) and its mechanical effect on the glial cells of the nerve and its axons.

While the invention has been shown in only a few of its forms, it should be apparent to those skilled in the art that it is not so limited but susceptible to various changes without departing from the scope of the invention.

What is claimed is:

1. A method for producing a non-human mammalian model for neurogenic pain, comprising the step of:
   altering a peripheral nerve of a non-human mammal by non-surgically placing a gel substance into the fascial tunnel through which the peripheral nerve passes, wherein the placement of the gel substance leads to one or more pain behaviors selected from mechanical allodynia and mechanical hyperalgesia, thereby producing a non-human mammalian model for neurogenic pain.

2. The method of claim 1, wherein the peripheral nerve is a peripheral spinal nerve or a spinal lumbar nerve root.

3. The method of claim 2, wherein the peripheral spinal nerve is selected from the group consisting of a tibial nerve, a peroneal nerve, a saphenous nerve and a sciatic nerve.

4. The method of claim 2, wherein the spinal lumbar nerve root is lumbar 4 (L4) or lumbar 5 (L5) nerve root.

5. The method of claim 1, wherein the gel substance comprises collagen, hydrogel or both.

6. The method of claim 1, wherein the pain behavior of mechanical allodynia is static mechanical allodynia, dynamic mechanical allodynia or both.

7. A non-human mammalian model for neurogenic pain, wherein a peripheral nerve in the mammal has been altered by non-surgically placing a gel substance into the fascial tunnel through which the peripheral nerve passes, wherein the placement of the gel substance leads to one or more pain behaviors selected from mechanical allodynia and mechanical hyperalgesia.

8. The non-human mammalian model of claim 7, wherein the peripheral nerve is a peripheral spinal nerve or a spinal lumbar nerve root.

9. The non-human mammalian model of claim 8, wherein the peripheral spinal nerve is selected from the group consisting of a tibial nerve, a peroneal nerve, a saphenous nerve and a sciatic nerve.

10. The non-human mammalian model of claim 8, wherein the spinal lumbar nerve root is lumbar 4 (L4) or lumbar 5 (L5) nerve root.

11. The non-human mammalian model of claim 7, wherein the gel substance comprises collagen, hydrogel or both.

12. The non-human mammalian model of claim 7, wherein the pain behavior of mechanical allodynia is static mechanical allodynia, dynamic mechanical allodynia or both.

13. A method for screening a therapeutic agent for efficacy in treating neurogenic pain, comprising the steps of:
   a) producing a non-human mammalian model for neurogenic pain according to the method of claim 1;
   b) obtaining pain behavior of the mammalian model, wherein such pain behavior is pre-treatment pain behavior;
   c) administering a therapeutic agent to the mammalian model; and
   d) obtaining pain behavior of the mammalian model administered with the therapeutic agent, wherein such pain behavior is post-treatment pain behavior;
   wherein an alteration identified as reduced mechanical allodynia, reduced mechanical hyperalgesia, or reduced mechanical allodynia and mechanical hyperalgesia in the post-treatment pain behavior as compared to the pre-treatment pain behavior is indicative of efficacy of the therapeutic agent in treating neurogenic pain.

14. A method for screening a treatment for efficacy in treating neurogenic pain, comprising the steps of:
   a) producing a non-human mammalian model for neurogenic pain according to the method of claim 1;
   b) obtaining pain behavior of the mammalian model, wherein such pain behavior is pre-treatment pain behavior;
   c) conducting a treatment on the mammalian model; and
   d) obtaining pain behavior of the mammalian model after the treatment, wherein such pain behavior is post-treatment pain behavior;
   wherein an alteration identified as reduced mechanical allodynia, reduced mechanical hyperalgesia, or reduced mechanical allodynia and mechanical hyperalgesia in the post-treatment pain behavior as compared to the pre-treatment pain behavior is indicative of efficacy of the treatment in treating neurogenic pain.

15. A method for screening an analgesic agent for analgesic effect in neurogenic pain, comprising the steps of:
   a) producing a non-human mammalian model for neurogenic pain according to the method of claim 1;
   b) obtaining pain behavior of the mammalian model, wherein such pain behavior is pre-analgesic pain behavior;
   c) administering an analgesic agent to the mammalian model; and
   d) obtaining pain behavior of the mammalian model administered with the analgesic agent, wherein such pain behavior is post-analgesic pain behavior;

wherein an alteration identified as reduced mechanical allodynia, reduced mechanical hyperalgesia, or reduced mechanical allodynia and mechanical hyperalgesia in the post-analgesic pain behavior as compared to the pre-analgesic pain behavior is indicative of analgesic effect of the analgesic agent in neurogenic pain.

* * * * *